United States Patent
Martin et al.

(10) Patent No.: US 10,024,767 B2
(45) Date of Patent: Jul. 17, 2018

(54) SYSTEMS AND METHODS FOR COLLECTION AND SAMPLING OF CHEMICAL SPECIES

(71) Applicant: TIAX LLC, Lexington, MA (US)

(72) Inventors: John F. Martin, Wilmington, MA (US); John R. Powell, Arlington, MA (US); Daniel J. Ehntholt, Hudson, MA (US); Paul Michael Drennan, Westford, MA (US); Michael Jakubowski, Loudon, NH (US); Madeline McComish, Everett, MA (US)

(73) Assignee: TIAX LLC, Lexington, MA (US)

( * ) Notice: Subject to any disclaimer, the term of this patent is extended or adjusted under 35 U.S.C. 154(b) by 142 days.

(21) Appl. No.: 14/910,719

(22) PCT Filed: Aug. 8, 2014

(86) PCT No.: PCT/US2014/050305
§ 371 (c)(1),
(2) Date: Feb. 8, 2016

(87) PCT Pub. No.: WO2015/021363
PCT Pub. Date: Feb. 12, 2015

(65) Prior Publication Data
US 2016/0195456 A1 Jul. 7, 2016

Related U.S. Application Data (60) Provisional application No. 61/958,941, filed on Aug. 8, 2013.

(51) Int. Cl.
*G01N 1/10* (2006.01)
*G01N 1/02* (2006.01)
(Continued)

(52) U.S. Cl.
CPC ............. *G01N 1/10* (2013.01); *G01N 1/02* (2013.01); *G01N 1/28* (2013.01); *G01N 1/30* (2013.01);
(Continued)

(58) Field of Classification Search
CPC .... G01N 1/02; G01N 2001/028; G01N 19/04; G01N 1/28; G01N 1/30; G01N 1/4077;
(Continued)

(56) References Cited

U.S. PATENT DOCUMENTS 4,787,380 A * 11/1988 Scott .................... A61F 13/023
206/440
5,082,706 A * 1/1992 Tangney .............. C09D 183/08
428/352
(Continued)

FOREIGN PATENT DOCUMENTS

WO     2008096225 A2    8/2008

OTHER PUBLICATIONS

Supplementary European Search Report, European Application No. 14 83 3592, dated Mar. 31, 2017, 9 pages.
(Continued)

*Primary Examiner* — Jennifer Wecker
(74) *Attorney, Agent, or Firm* — Cantor Colburn LLP (57) ABSTRACT

A method for collecting a compound from a surface, the method comprising providing a silicone adhesive collector comprising a silicone adhesive layer on a backing; contacting the silicone adhesives collector and a first solvent to provide a wetted collector; contacting the silicone adhesive layer of the silicone adhesive collector and a surface to be analyzed to provide a loaded collector; and removing the loaded collector from the surface to collect the compound. The disclosure also relates to a system for collecting a chemical compound from surfaces, the system comprising a
(Continued)

silicone adhesive collector comprising a backing, and a silicone adhesive layer disposed on the backing; a first solvent; and instructions to dispose the first solvent on the silicone adhesive collector, the surface, or a combination thereof.

35 Claims, 2 Drawing Sheets

(51) Int. Cl.
  *G01N 1/28*     (2006.01)
  *G01N 19/04*    (2006.01)
  *G01N 1/30*     (2006.01)
  *G01N 33/38*    (2006.01)
  *G01N 1/40*     (2006.01)
  *B01L 3/00*     (2006.01)
  *G01N 1/00*     (2006.01)

(52) U.S. Cl.
  CPC ........... *G01N 19/04* (2013.01); *G01N 33/383* (2013.01); *B01L 3/508* (2013.01); *B01L 3/5029* (2013.01); *B01L 3/5082* (2013.01); *B01L 3/50825* (2013.01); *B01L 2300/042* (2013.01); *B01L 2300/0809* (2013.01); *B01L 2300/0851* (2013.01); *G01N 1/4077* (2013.01); *G01N 2001/007* (2013.01); *G01N 2001/028* (2013.01); *G01N 2001/2833* (2013.01); *G01N 2001/4083* (2013.01)

(58) Field of Classification Search
  CPC ..... G01N 2001/007; G01N 2001/2833; G01N 2001/4083; G01N 21/76; G01N 21/78; G01N 21/783; G01N 2800/323; G01N 31/22; G01N 31/223; G01N 33/182; G01N 33/1846; G01N 33/487; G01N 33/49; G01N 33/54366; G01N 33/558; G01N 33/6827; G01N 33/6839; G01N 33/92; B01L 2200/0668; B01L 2200/0689; B01L 2300/042; B01L 2300/046; B01L 2300/047; B01L 2300/049; B01L 2300/0809; B01L 2300/0851; B01L 2400/043; B01L 2400/0683; B01L 2400/0694; B01L 3/50215; B01L 3/5029; B01L 3/508; B01L 3/5082; B01L 3/50825
  See application file for complete search history.

(56) References Cited

U.S. PATENT DOCUMENTS

| | | | |
|---|---|---|---|
| 6,306,412 B1 * | 10/2001 | Crotty ................. | A61K 8/0208 424/10.1 |
| 2005/0211580 A1 * | 9/2005 | Kaszubski ............... | C08J 5/124 206/223 |
| 2006/0216196 A1 * | 9/2006 | Satoh .................... | B01L 3/5029 422/400 |
| 2008/0115595 A1 | 5/2008 | Duval | |
| 2008/0188387 A1 * | 8/2008 | Horsewood ............ | A61B 10/02 510/130 |
| 2009/0298995 A1 * | 12/2009 | Krawinkel .............. | C08L 53/02 524/505 |
| 2011/0060099 A1 | 3/2011 | Ahn et al. | |
| 2012/0193769 A1 * | 8/2012 | Liu ...................... | H01L 21/2225 257/655 |
| 2013/0089890 A1 * | 4/2013 | Pflanz .................... | B01L 3/508 435/34 |

OTHER PUBLICATIONS

BIORE: Ultra Deep Cleansing Pore Strips, Aug. 15, 2012, retrieved on Oct. 2, 2014, retrieved from the Internet URL: https://web.archive.org/web/20120815030426/http://www.biore.com/en-US/deep-cleansing-product-family/pore-strips?#ultra.

International Search Report for International Application No. PCT/US2014/050305, international filing date of Aug. 8 2014, dated Nov. 14, 2014, 7 pages.

Written Opinion for International Application No. PCT/US2014/050305, international filing date of Aug. 8, 2014, dated Nov. 14, 2014, 6 pages.

* cited by examiner

SYSTEMS AND METHODS FOR COLLECTION AND SAMPLING OF CHEMICAL SPECIES

CROSS-REFERENCE TO RELATED APPLICATIONS

This application is a U.S. national stage application of International Application No. PCT/US2014/050305 entitled "SYSTEMS AND METHODS FOR COLLECTION AND SAMPLING OF CHEMICAL SPECIES", which has an international filing date of 8 Aug. 2014, and which claims priority to U.S. Provisional Patent Application No. 61/958,941, filed 8 Aug. 2013, the contents of which are incorporated herein by reference in their entirety.

This invention was made with government support under contract number D11PC20244 awarded by the Department of Homeland Security. The government has certain rights in the invention.

BACKGROUND

(1) Technical Field

This disclosure relates generally to the field of sampling and collecting trace amounts of volatile and non-volatile chemical species from surfaces, and the related methodology.

(2) Description of the Related Art

The collection and analysis of chemical compounds from surfaces is used for a variety of purposes in both indoor and outdoor environments. Collection from surfaces can be used to show the presence and/or an amount of a selected compound on a surface. For example, in environmental assessments, collections are used to evaluate the effectiveness of remedial progress and for regulatory compliance. Collection protocols are used for post-decontamination sampling and spill clean-up verification of environmental contaminants. Collection techniques are used to test for contaminants such as lead on household surfaces and for post-remediation analysis of methamphetamine houses. For occupational applications, surface collections are used for industrial hygiene and occupational exposure analysis. Dermal wipe methods are used on hands to monitor personal human exposure to pesticides. Homeland security-related applications at airports and borders use these techniques to screen for explosives. Collection techniques are used in forensic applications to collect potential evidence at crime scenes and incidents involving national security.

The sampling or collection of chemical compounds from a surface can be accomplished in a variety of ways. One method of collection is called "wipe sampling". In wipe sampling, a selected area is wiped with a wiping media and then the wipe is subsequently analyzed for the compounds of interest. Although this method is widely employed, there are a number of drawbacks. Most wipe sampling methods are a manual process and the pressure applied can vary widely by field operator. Also, wipe sampling is restricted to smooth, non-porous surfaces because porous and textured surfaces can have insufficient collection yields from wipe sampling. However, many surfaces targeted for collection are porous, textured, and three dimensional. In addition, current collection materials are suspected as being a source of contamination. For example, cotton gauze, a common wipe material, is suspected as being a source of contamination and subsequent cross-contamination during collection. In addition, the materials and processes used in current wiping protocols vary widely and can lead to lab-to-lab differences making it difficult to compare results generated from different groups.

Another method of collection is called chip sampling. Chip sampling is appropriate for porous surfaces, such as concrete. In chip sampling, a cleaned chisel or hammer is used to remove a physical sample from the target surface for subsequent analysis. Chip sampling is a destructive collection method that has a significant drawback as it is often difficult or undesirable to remove a physical sample from a surface. For example, the surface may be on an object having a high value or having symbolic importance, and thus alteration would be highly undesirable.

Another technique of collection is ion mobility spectroscopy. Ion mobility spectroscopy uses a wipes approach and is used to screen for explosives and narcotics at airports. Ion mobility spectroscopy is limited to analyzing for specific compounds and can require prolonged screening reset times.

Another technique, ambient ionization mass spectrometry, can be used to analyze certain chemical compounds on surfaces. However operating a mass spectrometer in the field can be time consuming, complex, and costly.

A new method that is under development is a vacuum-extraction solid phase microextraction device that samples the headspace on exposed surfaces. A limitation of this method is that low volatility compounds require extended sampling times. This approach is not yet commercially available.

Thus the remains a need for an effective method of collecting chemical compounds from surfaces, in particular porous and textured surfaces.

SUMMARY

A method for collecting a compound from a surface comprises providing a silicone adhesive collector comprising a silicone adhesive layer on a backing; contacting the silicone adhesives collector and a first solvent to provide a wetted collector; contacting the silicone adhesive layer of the silicone adhesive collector and a surface to be analyzed to provide a loaded collector; and removing the loaded collector from the surface to collect the compound.

A system for collecting a chemical compound from a surfaces comprises a silicone adhesive collector comprising a backing, and a silicone adhesive layer disposed on the backing; a first solvent; and instructions to dispose the first solvent on the silicone adhesive collector, the surface, or a combination thereof.

The above described and other features are exemplified by the following Detailed Description, Examples, Claims, and Figures.

BRIEF DESCRIPTION OF THE DRAWINGS

Referring now to the figures, in which like elements are numbered alike.

DETAILED DESCRIPTION

Disclosed is a system for collecting a chemical compound from a surface, the system comprising a silicone adhesive collector comprising a backing 20 and silicone adhesive layer 10 disposed on the backing; and a solvent. Also disclosed is a method for collecting a compound from a surface, the method comprising: providing a silicone adhesive collector comprising a silicone adhesive layer on a backing; contacting a silicone adhesive collector and a first solvent to provide a wetted collector; contacting the silicone adhesive layer of the silicone adhesive collector and a surface to be analyzed to provide a loaded collector; and removing the loaded collector from the surface to collect the compound. The loaded collector may then be analyzed to determine a content of the compound on the surface.

In an embodiment, the silicone adhesive collector comprises a non-tacky backing material and a silicone adhesive layer comprising a silicone adhesive on the backing. The silicone adhesive exhibits suitable adhesive properties and may be a platinum cured polydimethylsiloxane (PDMS), for example. Collectors with a range of tackiness from low to high tack have shown performance superior to gauze when used in the method described below. Higher tack can provide improved collection performance; however, for ease of use a lower tack adhesive can be desirable.

The silicone adhesive collector, and the related methodology disclosed herein, is advantageous in that it can collect and preserve trace amounts of volatile and nonvolatile compounds that may be present on a surface. Representative compounds that can be collected by the collector include pesticides, toxins, explosives, contraband compounds. For example, the collector is suitable for collection of parathion, fenthion diisopropyl methyl phosphonate, methyl salicylate, diethanolamine, nicotine, and malathion.

The silicone-based adhesive material allows the collector to be used on vertical, inverted, uneven, heavily soiled, or difficult-to-adhere-to surfaces. While not wanting to be bound by theory, it has been unexpectedly found that the silicone adhesive collector has more intimate contact with the surface resulting in higher collection yields, permitting more efficient and reproducible extraction, collection, concentration, recovery, and analysis of trace compounds that may be present in or on surfaces. Further, when used in combination with the solvent, unexpected improvements in collection efficiency are provided. Further still, it has been unexpectedly found that certain backings provide synergistic effects with the silicone adhesive and/or the solvent, providing further improvements in collection efficiency. The silicone adhesive collector and related methodology yields a more effective method for the sampling and analysis of surfaces for volatile or non-volatile chemical compounds, such as toxic industrial chemicals or chemical warfare agents. The results obtained from this approach can be used for subsequent legal proceedings and also to verify cleanliness of surfaces after decontamination procedures have been applied.

A purpose of the backing material of the collector is to provide mechanical support and suitable handling properties. The backing may be permeable or non-permeable to air, the solvent, or a combination thereof. Representative permeable backing materials include natural materials and synthetic polymeric materials, such as a silicone (e.g., a silicone elastomer or rubber), a polytetrafluoroethylene, a polyurethane, a polyester, a polyamide, a polyolefin such as polyethylene or a polypropylene and copolymers thereof, or a combination thereof. Examples of polymers that may be suitable for use in the backing include epoxies, ethylene propylene diene rubber (EPR), ethylene propylene diene monomer rubber (EPDM), melamines, polyacetals, polyacrylics such as polyacrylic acid, polyacrylonitriles, polyamides including polyamideimide, polyarylene ethers, polyarylene sulfides, polyarylene sulfones, polybenzoxazoles, polybenzothiazole, polybutadienes and copolymers thereof, polycarbonates, polycarbonate esters, polyether ketones, polyether ether ketones, polyether ketone ketones, polyethersulfones, polyesters, polyimides such as polyetherimides, polyisoprenes and copolymers thereof, polyphosphazenes, poly(alkyl) (meth)acrylates, polystyrenes and copolymers thereof, rubber-modified polystyrenes such as acrylonitrile-butadiene-styrene (ABS), styrene-ethylenebutadiene (SEB), and methyl methacrylate-butadiene-styrene (MBS), polyoxadiazoles, polysilazanes, polysulfones, polysulfonamides, polyvinyl acetates, polyvinyl chlorides, polyvinyl esters, polyvinyl ethers, polyvinyl halides, polyvinyl nitriles, polyvinyl thioethers, and polyureas. A combination comprising at least one of the foregoing polymers can be used. In an embodiment the polymer is a silicone elastomer. Representative commercially available materials include the Mylan Industries products Medifilm 437, which is described as an aliphatic polyether polyurethane, and Medifilm 426, which is described as a hydrophilic polyurethane, the Polymer Science, Inc. products PS Silicone 1033, which is described as a silicone elastomer, and PS 1082 which is described as a polyether polyurethane, the CS Hyde Company product CS Hyde, which is described as a silicone elastomer, and the Wacker Silicones product Wacker Si Elastosil Film which is described as a silicone elastomer film. The backing material may be a non-tacky silicone elastomer, a flexible polymer such as a polyurethane or polyamide, or a semi-interpenetrating network (IPN) comprising a polymer such as polytetrafluoroethylene (PTFE).

Alternatively, a non-permeable backing material comprising a metal, glass, a polymeric material, or a combination thereof can be used. Representative non-permeable backing materials include metal foils, glass sheets, or a combination thereof. The metal may comprise Al, Cu, Fe, Ni, an alloy thereof, or a combination thereof. Aluminum foil is specifically mentioned.

The backing may have any suitable form and may be woven or nonwoven. A multi-layer backing may be used. The backing may have a total thickness of 0.01 millimeters (mm) to 2 mm, 0.02 mm to 1.5 mm, or 0.04 mm to 1 mm. The backing may be tacky or non-tacky. A non-tacky backing is specifically mentioned.

The silicone adhesive is disposed on the backing to provide a silicone adhesive layer. The silicone adhesive may be a crosslinked polyorganosiloxane such as a platinum cured polydimethylsiloxane (PDMS) or polymethylphenylsiloxane having, for example, 5 to 15,000 units.

In an embodiment, the silicone adhesive is the crosslinked product of a composition comprising an ethylenically unsaturated organopolysiloxane, a —SiH containing organopolysiloxane, and a hydrosilylation catalyst. The ethylenically unsaturated organopolysiloxane comprises a group that can undergo hydrosilylation, e.g., a vinyl or alkenyl group. The ethylenically unsaturated organopolysiloxane may comprise structural units having average Formula 1 wherein a may be 1-4. The $R^1$ group may comprise H, a substituted or unsubstituted $C_2$ to $C_{20}$ alkenyl, a substituted or unsubstituted (meth)acryloxyalkyl, cyano, a substituted or unsubstituted cyano-functional group, a substituted or unsubstituted alkyl, a substituted or unsubstituted cycloalkyl, a substituted or unsubstituted aryl, a substituted or unsubstituted alkylaryl, a substituted or unsubstituted halogenated hydrocarbon group, a substituted or unsubstituted alkyloxypoly(oxyalkylene) group, a substituted or unsubstituted alkenyloxypoly(oxyalkylene) group, a substituted or unsubstituted alkoxy group, a substituted or unsubstituted aminoalkylgroup, a substituted or unsubstituted ester-containing, a substituted or unsubstituted hydroxyl-containing group, a substituted or unsubstituted isocyanate-containing group, a substituted or unsubstituted-containing aldehyde group, a substituted or unsubstituted anhydride-containing group, a substituted or unsubstituted carboxylic acid-containing group, or a combination thereof, with the proviso that at least one of $R^1$ is an ethylenically unsaturated group, and preferably wherein each molecule has an average of two ethylenically unsaturated groups per molecule.

Representative ethylenically unsaturated groups include vinyl, allyl, and hexenyl groups, or a combination thereof. The alkyl group may comprise a substituted or unsubstituted methyl, ethyl, propyl, isopropyl, n-butyl, s-butyl, t-butyl, pentyl, neopentyl, hexyl, octyl, undecyl, an octadecyl group, or a combination thereof. The aryl group may comprise a substituted or unsubstituted phenyl, tolyl, xylyl, benzyl, or 2-phenylethyl group, or a combination thereof. A halogenated hydrocarbon group, such as a 3,3,3-trifluoropropyl, 3-chloropropyl, dichlorophenyl, or a 6,6,6,5,5,4,4,3,3-nonafluorohexyl groups, or a combination thereof, may be included. The cyano-functional group may include a cyanoalkyl groups such as a cyanoethyl or a cyanopropyl groups, or a combinations thereof. The alkyloxypoly(oxyalkyene) group may include propyloxy(polyoxyethylene), propyloxypoly(oxypropylene), propyloxy-poly(oxypropylene)-co-poly(oxyethylene), or a combination thereof. A halogenated alkyloxypoly(oxyalkyene) group may include perfluoropropyloxy(polyoxyethylene), perfluoropropyloxy-poly(oxypropylene), perfluoropropyloxy-poly(oxypropylene) copoly(oxyethylene), or a combination thereof. The alkenyloxypoly(oxyalkyene) group may include allyloxy-poly(oxyethylene), allyloxypoly(oxypropylene), allyloxy-poly(oxypropylene) copoly(oxyethylene), or a combination thereof. The alkoxy group may include methoxy, ethoxy, n-propoxy, isopropoxy, n-butoxy, ethylhexyloxy, or a combination thereof. The aminoalkyl group may include 3-aminopropyl, 6-aminohexyl, 1,1-diaminoundecyl, 3-(N-allylamino)propyl, N-(2-aminoethyl)-3-aminopropyl, N-(2-aminoethyl)-3-aminoisobutyl, p-aminophenyl, 2-ethylpyridine, 3-propylpyrrole, or a hindered aminoalkyl group such as a tetramethylpiperidinyl oxypropyl group, an epoxyalkyl group such as a 3-glycidoxypropyl, 2-(3,4,-epoxycyclohexyl)ethyl, or a 5,6-epoxyhexyl group. The ester-containing group may include acetoxymethyl, benzoyloxypropyl, or a combination thereof. The hydroxyl-containing group may include hydroxy, 2-hydroxyethyl group, or a combination thereof. The isocyanate-containing group may include 3-isocyanatopropyl, tris-3-propylisocyanurate, propyl-t-butylcarbamate, propylethylcarbamate, or a combination thereof.

The aldehyde-containing group may include undecanal or a butyraldehyde group. The anhydride-containing group may include 3-propyl succinic anhydride, 3-propyl maleic anhydride, or a combination thereof. The carboxylic acid-containing group may include 3-carboxypropyl, 2-carboxyethyl, 10-carboxydecyl, or a combination thereof, or metal salts of a carboxylic acid group such as zinc, sodium, or potassium salt of 3-carboxypropyl and 2-carboxyethyl groups. A combination comprising at least one of the foregoing may be used.

In an embodiment, the ethylenically unsaturated organopolysiloxane is an alkenyl-substituted polydiorganosiloxane, and at least 50 percent of the organic groups in the alkenyl-substituted polydiorganosiloxane may be alkyl groups, for example methyl groups. Examples of the ethylenically unsaturated organopolysiloxane include polydimethysiloxane-polymethylvinylsiloxane copolymers, hexenyldimethylsiloxy-terminated polydimethylsiloxane-polymethylhexenylsiloxane copolymers, hexenyldimethylsiloxy-terminated polydimethylsiloxane polymers, vinyldimethylsiloxy-terminated polydimethylsiloxane polymers, vinyl or hexenyldimethylsiloxy-terminated poly(dimethylsiloxane-silicate) copolymers, mixed trimethylsiloxy-vinyldimethylsiloxy terminated poly(dimethylsiloxane-vinylmethylsiloxane-silicate) copolymers, vinyl or hexenyldimethylsiloxy terminated poly(dimethylsiloxane-hydrocarbyl) copolymers, derivatives thereof, and combinations thereof. Functional groups may be present at any point in the ethylenically unsaturated organopolysiloxane, for example, in the middle of the polymer or as an endgroup(s). Functional groups, such as diorgano-, —OH, -vinyl, -hexenyl, -epoxy, or -amine groups may be used in the ethylenically unsaturated organopolysiloxanes contemplated herein. End groups such as trimethyl ($Me_3$), diphenylmethyl ($Ph_2Me$), or dimethylphenyl ($Me_2Ph$) may or may not be present in the organopolysiloxane.

The ethylenically unsaturated organopolysiloxane may comprise 1 to 10,000, or 4 to 8,000, or 8 to 6,000 structural units. The ethylenically unsaturated organopolysiloxane may have a viscosity at 25° C. of 1 to 100,000 square millimeters per second ($mm^2/s$), or 100 to 80,000 $mm^2/s$. A combination of different ethylenically unsaturated organopolysiloxanes can be used.

The —SiH containing organopolysiloxane may comprise structural units having the average Formula 2:

wherein a may be 1 to 4, and $R^2$ may be the same as is disclosed above for $R^1$ for the ethylenically unsaturated organopolysiloxane with the proviso that at least one of $R^2$ is H and the ethylenically unsaturated group need not be present. In an embodiment no ethylenically unsaturated group is present.

The —SiH containing organopolysiloxane may comprise 1 to 10,000, or 4 to 8,000, or 8 to 6,000 structural units. The —SiH containing organopolysiloxane may have a viscosity at 25° C. of 1 to 10,000 square millimeters per second ($mm^2/s$), or 1 to 8,000 $mm^2/s$, or 1 to 6,000 $mm^2/s$. A combination of different —SiH containing organopolysiloxanes can be used.

In an embodiment, the content of the ethylenically unsaturated organopolysiloxane and the —SiH containing organopolysiloxane may be selected such that the ratio of total moles of Si—H groups:reactive ethylenically unsaturated groups ("RH:Alk") is in the range of 0.1 to 30 (i.e., H:alkenyl=1:10 to 30:1), or 0.3 to 15, or 0.5 to 5, or 0.8 to 2, or 0.8 to 1.7.

In a more specific embodiment, the silicone adhesive may be a gel, for example a gel as described in GB849885, GB1582081, US40720635, U.S. Pat. No. 5,145,933, EP0324411, EP0396246, and WO/2013/056077. As used herein, silicone gels can have a viscosity of, for example, 100,000 centiPoise (cP) to 5,000,000 cP, specifically 100,000 cP to 1,000,000 cP, more specifically 100,000 cP to 500,000 cP, each measured at 25° C. As is known in the art, gels can be obtained by manipulation of the ratios of alkenyl to —SiH groups, the degree of crosslinking in the gel, and the viscosity of the components of the composition used to produce the gel. For example, in an embodiment, the —SiH containing organopolysiloxane may comprise (a) an organopolysiloxane comprising at least three —SiH groups per molecule and comprising $R^2{}_2XSiO_{1/2}$ terminal groups, $R^2HSiO_{2/2}$ units, and optionally $R^2{}_2SiO_{2/2}$ units, wherein each $R^2$ is the same or different, and is the same as defined in Formula (2), and X is H or $R^2$; and (b) an —Si—H terminated organopolysiloxane comprising $R^2HSiO$ terminal groups and $R^2{}_2SiO_{2/2}$ units, wherein each $R^2$ is the same or different, and is the same as defined in Formula (2). Preferably, in both organopolysiloxanes (a) and (b), each $R^2$ is the same or different, and is a $C_1$ to $C_8$ alkyl, a $C_1$ to $C_8$ perfluoroalkyl, or a $C_6$ to $C_{12}$ aryl. In a preferred embodiment, the organopolysiloxane (a) consists essentially of, or consists of, at least three —SiH groups per molecule and comprises $R^2{}_2XSiO_{1/2}$ terminal groups, $R^2HSiO_{2/2}$ units, and $R^2{}_2SiO_{2/2}$ units, wherein each $R^2$ is the same or different, and is a $C_1$ to $C_8$ alkyl, a $C_1$ to $C_8$ perfluoroalkyl, or a $C_6$ to $C_{12}$ aryl, and X is H or $R^2$; and the —Si—H terminated organopolysiloxane (b) consists essentially of, or consists of, $R^2HSiO$ terminal groups and $R^2{}_2SiO_{2/2}$ units, wherein each $R^2$ is the same or different, and is a $C_1$ to $C_8$ alkyl, a $C_1$ to $C_8$ perfluoroalkyl, or a $C_6$ to $C_{12}$ aryl. In this embodiment, a mole percent of the —SiH groups provided by the —SiH terminated organopolysiloxane (b) relative to the total moles of —SiH groups ("RH(C)") is 10% to 99%, or 60% to 99%, 70% to 99%, or 80% to 99%, or 85% to 95%. Further in this embodiment, RH:Alk may be as described above, and preferably is in the range of 0.1 to 10, or 0.3 to 8, or 0.5 to 5, or 0.8 to 2, or 0.8 to 1.7. An embodiment in which RH(C) is 80% to 99%, or 85% to 95%, and RH:Alk is 0.8 to 2, or 0.8 to 1.7 is mentioned.

The silicone adhesive also comprises a hydrosilylation catalyst. Suitable hydrosilylation catalysts include, but are not limited to, platinum catalysts such as chloroplatinic acid, alcohol solutions of chloroplatinic acid, dichlorobis(triphenylphosphine)platinum(ll), platinum chloride, platinum oxide, complexes of platinum compounds with unsaturated organic compounds such as olefins, complexes of platinum compounds with organosiloxanes containing unsaturated hydrocarbon groups, such as Karstedts catalyst (i.e. a complex of chloroplatinic acid with 1,3-divinyl-1,1,3,3-tetramethyldisiloxane) and 1,3-diethenyl-1,1,3,3-tetramethyldisiloxane, and complexes of platinum compounds with organosiloxanes, wherein the complexes are embedded in organosiloxane resins. For example, a hydrosilylation catalyst may comprise a 0.5% platinum containing platinum-divinyltetramethyldisiloxane (a complex that is commercially available from Dow Corning Corporation in Midland, Mich.). The hydrosilylation catalyst may be added to the composition in an amount sufficient to provide, for example, 1 to 30 ppm of platinum based on the weight of the silicone composition.

The silicone adhesive may be selected to provide a desirable tack. While not wanting to be bound by theory, it is understood that collection efficiency is related to a tack of the silicone adhesive. Tack may be determined according to the PSTC-6 Tack Rolling Ball method as defined by the Pressure Sensitive Tape Council Inc., the content of which is incorporated herein by reference in its entirety. In an embodiment, the silicone adhesive provides a tack of 5 mm to 100 mm, or 10 mm to 75 mm, or 20 mm to 70 mm, or 30 mm to 65 mm when determined according to the PSTC-6 Tack Rolling Ball method and using a steel ball. In another embodiment, the silicone adhesive provides a tack of 0 mm to 50 mm, or 2 mm to 40 mm, or 4 mm to 30 mm, or 6 mm to 25 mm when determined according to the PSTC-6 Tack Rolling Ball method and using a nylon ball. Alternatively, tack may be determined according to the PSTC-101 Peel Adhesion of Pressure Sensitive Tape method as defined by the Pressure Sensitive Tape Council, the content of which is incorporated herein by reference in its entirety. In an embodiment, the silicone adhesive provides a tack of 5 to 1500 grams-force-inch, or 50 to 300 grams-force-inch, when determined on concrete brick according to the PSTC-101 Peel Adhesion of Pressure Sensitive Tape method.

The silicone adhesive is disposed on the backing and cured to provide a silicone adhesive layer 10. The silicone adhesive may be disposed on the backing by any suitable method, such as coating, casting, dipping, or spraying. A thickness of the silicone adhesive layer may be 0.1 millimeter (mm) to 3 mm, 0.2 mm to 2.5 mm, or 0.4 mm to 2 mm. While not wanting to be bound by theory, it is believed that thicker adhesive layers provide improved collection efficiency. However, if the adhesive layer is too thick, the collector is mechanically unstable. One or more intermediate layers can be present between the backing and the adhesive layer, for example a primer or a tie layer.

The solvent may be disposed in the silicone adhesive, or may be provided separately from the silicone adhesive collector. The solvent may be disposed on the silicon adhesive collector, the surface to be analyzed, or combination thereof during collection. While not wanting to be bound by theory, it is understood that contacting the surface to be analyzed with the solvent enhances or increases the collection efficiency and/or collection yield. In an embodiment the solvent is applied to a porous backing of the silicone adhesive collector. In yet another embodiment the solvent is applied to the silicone adhesive collector by dipping the collector in the solvent.

The solvent may be a hydrocarbon, such as a C1 to C10 or C2 to C8 hydrocarbon. Representative examples of the organic solvent include alcohols (e.g., ethanol, hexanol); aldehydes (e.g., acetaldehydes, propionaldehydes), ketones (e.g., acetone, methyl ethyl ketone); esters (e.g., ethyl acetate), ethers (e.g., diisobutyl ether), amides (e.g., dimethyl formamide, N-methylpyrrolidinone), aliphatic hydrocarbons (e.g., hexane), aromatic hydrocarbons (e.g., toluene), acetonitrile; sulfoxides (e.g., dimethylsulfoxide); sulfones (e.g., diethyl sulfone), water, or a combination comprising at least one of the foregoing solvents. Hexane, ethyl acetate, methyl acetate, and isopropanol are specifically mentioned. A combination of hexanes is also mentioned. Varying the solvent used may enhance collection for certain chemical target-surface combinations.

Figure 1A:
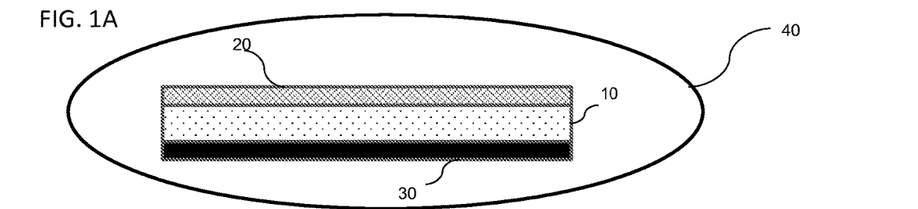
FIG. 1A illustrates an embodiment of a silicon adhesive collector, including a backing 20, a silicon adhesive layer 10, a release layer 30, and a package 40.
Figure 1B:
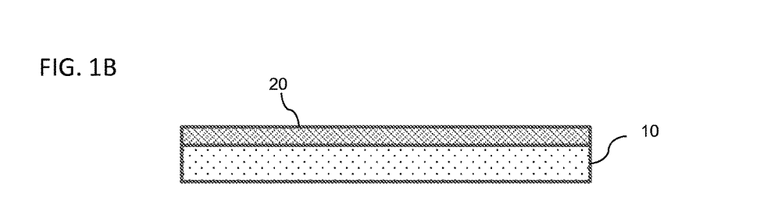
FIG. 1B illustrates an embodiment of a silicon adhesive collector after the release layer 30 has been removed.

As shown in FIG. 1A, the silicone adhesive collector, which comprises a silicone adhesive layer 10 on a backing 20, may further comprise a release layer 30 disposed on the silicone adhesive. Also, the silicone adhesive collector may be disposed in a package 40, such as a metallized foil envelope. The release layer may be designed to protect the silicone adhesive prior to use and to be removed by a user prior to collection. Shown in FIG. 1B is a silicone adhesive collector with the release layer 30 removed to provide the exposed silicone adhesive layer 10 on the backing 20. The release layer may comprise a polyester, polyethylene terephthalate, or a polypropylene, for example.

In an embodiment, a silicone adhesive of the silicon adhesive collector is a high purity, medical or food grade, silicone-based adhesive material. In another embodiment, a combination of the silicone-based collector and an organic solvent is used to enhance the collection efficiency or collection yield.

In an embodiment, the silicone adhesive collector can further comprise a release layer on the silicone adhesive. In use, release layer is removed, exposing the silicone adhesive layer, and then the silicone adhesive layer is contacted with a solvent, e.g. by spraying or dipping, to provide a wetted collector. The wetted collector may then be contacted to the surface targeted for collection. After a set time period, the collector is removed from the surface, and optionally used as a wipe on the surface, to complete the collection procedure. The collector may then be later analyzed, e.g. by standard analytical procedures such as gas chromatography-mass spectrometry (GC/MS), to determine the type and concentration of compounds that were collected.

The collector is effective for collecting a variety of compounds of different volatilities, including compounds different volatilities. Compounds having a vapor pressure of $1 \times 10^{-8}$ Pascal (Pa) to 0.8 atmosphere (80160 Pa), for example, can be effectively collected using the collector. Representative classes of compounds that can be effectively collected include pesticides, pollutants, drugs, toxins, explosives, contraband, halogenated solvents, or other compounds of interest. Examples of specific compounds include, but are not limited to, naphthalene, fluorene, anthracene, pyrene, benz(a)anthracene, benz(a)pyrene, biphenyl, and polychlorinated biphenyls such as decachlorobiphenyl, aldirn, diazinon, p,p'-dichlorodiphenyltrichloroethane, dieldrin, dimethoate, hexachlorobenzene, malathion, methyl-parathion, parathion, fenthion, diisopropyl methyl phosphonate, methyl salicylate, diethanolamine, nicotine, dibenzo-p-dioxins, and dibenzofurans, for example. In particular, the disclosed collector and method is suitable for collecting trace amounts, e.g., 0.0001 milligrams per square meter ($mg/m^2$) to 1 gram per square meter ($g/m^2$), or 0.001 $mg/m^2$ to 1 $g/m^2$, or 0.01 $mg/m^2$ to 1 $g/m^2$, or 0.1 $mg/m^2$ to 1 $g/m^2$ of such compounds.

Also, the collector and method are suitable for collecting compounds from a variety of surfaces. Representative surfaces include concrete, asphalt, furniture, wallboard, painted surfaces, textile surfaces, glass, leather, metal, rubber, skin, vinyl floor tiles, unglazed floor tiles, carpeting, polymeric and wood-based flooring, unfinished wood, plywood, composites, and polymeric or plastic surfaces.

Also disclosed is a system for collecting a chemical compound from a surface, the system comprising: a silicone adhesive collector comprising a backing, and a silicone adhesive layer disposed on the backing; a first solvent (which can be a mixture of solvents); and instructions to dispose the first solvent on the silicone adhesive collector, the surface, or a combination thereof. In an embodiment, the instructions can instruct disposing the first solvent on the silicone adhesive layer, the surface, or a combination thereof prior to contacting the silicone adhesive layer and the surface. In another embodiment, the system further comprises a second solvent. The system may include instructions which instruct disposing the second solvent on the silicone adhesive collector, the surface, or a combination thereof before or after disposing the first solvent. For example, the instructions may instruct disposing the first solvent on the backing of the collector and disposing the second solvent on the surface to be analyzed prior to contacting the silicone adhesive layer and the surface.

In an embodiment, disclosed is a method for collecting a compound from a surface, the method comprising: contacting a silicone adhesive collector and a first solvent to provide a wetted collector; disposing the silicone adhesive collector on a surface to be analyzed to provide a loaded collector; and removing the loaded collector from the surface to collect the compound.

The first solvent may be disposed prior to or after the disposing of the silicone adhesive collector on the surface to be analyzed. For example, the first solvent may be disposed on the silicone adhesive layer of the silicone adhesive collector before the silicone adhesive collector is contacted with the surface to be analyzed. Alternatively, in an embodiment in which a backing which is porous to the solvent is used, the first solvent may be disposed on the porous backing. Alternatively, the first solvent may be disposed on the surface to be analyzed prior to contacting the surface with the silicone adhesive collector. In another embodiment, the first solvent is contained in the silicone adhesive of the silicone adhesive collector.

In another embodiment, a first and a second solvent can be used, wherein the first and second solvents may be the same or different. For example, the first solvent may be disposed on the silicone adhesive layer of the silicone adhesive collector before the silicone adhesive layer is contacted to the surface to be analyzed, and the second solvent may be contacted with the surface before contacting the surface with the silicone adhesive layer. In another embodiment, the silicone adhesive layer of the silicone adhesive collector may comprise the first solvent, and the second solvent may be disposed on the surface to be analyzed before contacting the surface with the silicone adhesive layer of the silicone adhesive collector. In yet another embodiment, the second solvent may be applied to a porous backing of the silicone adhesive collector before or after the silicone adhesive layer is contacted with the surface to be analyzed.

The solvent can be applied by any suitable method. Solvent application can be accomplished by spraying, coating, dropping with a metered pipette, by contacting with a moistened sponge or pad, by a brush, by contacting with a moistened foam roller, or by dipping the silicone adhesive collector in solvent, or combination thereof. In an embodiment, the solvent and silicone adhesive collector can be prepackaged together in a sealed unit dose package. For example, the collector can be pre-wetted with the solvent and ready for sampling when the package is opened. As is further disclosed above, use of methanol, ethanol, propanol, isopropanol, butanol, ethyl acetate, butanone, hexane, toluene, xylene, or a combination thereof is specifically mentioned.

Figure 2:
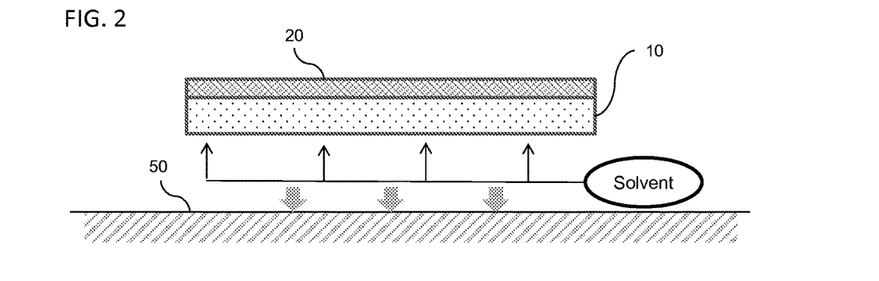
FIG. 2 illustrates an embodiment of a method of collecting a compound from a surface, wherein a solvent is disposed on the silicon adhesive layer 10 of the silicon adhesive collector prior to contacting the silicon adhesive collector to the target surface 50.

An embodiment of a method for collecting and sampling volatile and non-volatile chemical compounds from surfaces is shown in FIG. 2. Before collection the operator can identify and optionally delineate a selected area for analysis, e.g., an area that has been potentially exposed to targeted compounds. The targeted compound can be, or be derived from, a pesticide, toxin, explosive, contraband, or other compound of interest. To begin the collection, the silicone adhesive collector can be removed from its protective package 40 as shown in FIG. 1A, and held by the operator. The operator can then peel away the protective release layer 30, if present, exposing the silicone adhesive layer 10 of the collector. Next, the operator can apply the first solvent, e.g., isopropanol or hexane, to the silicone adhesive layer, the backing, the surface to be analyzed, or combination thereof. Also, in an embodiment wherein a second solvent is used, the second solvent may be applied to the silicone adhesive layer, the backing, the surface to be analyzed, or a combination thereof. An amount of the first and second solvents may each independently be 1 to 500 parts by weight, or 10 to 400 parts by weight, or 20 to 300 parts by weight, based on 100 parts by weight of a total weight of the silicone adhesive collector. The operator then contacts, e.g., places and adheres, the silicone adhesive layer of the silicon adhesive collector to the target surface 50. The silicone adhesive collector can be left in place for a selected time, e.g., for 1 second to 100 hours, or 10 seconds to 50 hours, or 20 seconds to 25 hours, or 40 seconds to 12 hours, and then the collector removed from the surface. If desired, the silicone adhesive collector can be used as a wipe on the surface as a final collection, and if desired the silicon adhesive collector can be folded. The collector can be later analyzed using any suitable method or analytical procedure, such as a procedure comprising gas chromatography, mass spectrometry, nuclear magnetic resonance spectroscopy, infrared spectroscopy, potentiometry, stripping voltammetry, atomic spectrometry, X-ray fluorescence, activation analysis, microscopy, thermal analysis, a hybrid method comprising at least one of the foregoing, or combination thereof, to determine characteristics of the target compound, such as a type or a concentration of a compound that was collected.

In an embodiment, the step whereby the collector is folded and used as a wipe is avoided. This variation of the method is considered a static collection since no wiping action is carried out.

Figure 3:
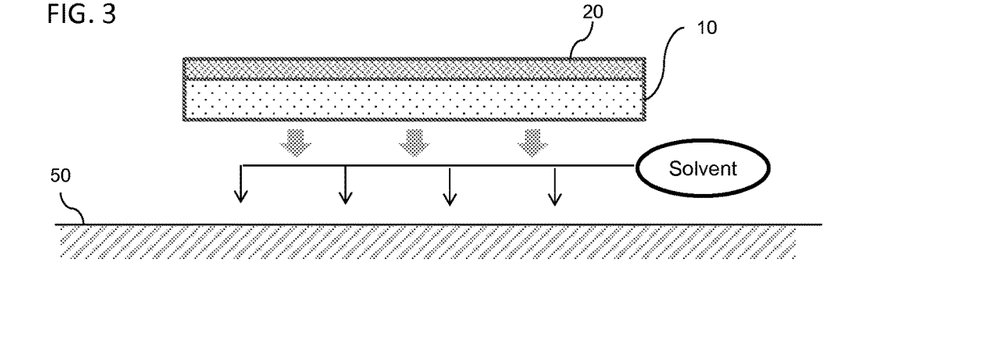
FIG. 3 illustrates another embodiment of a method of collecting a compound from a surface, wherein the solvent is applied to the target surface 50 prior to collection.

In the embodiment shown in FIG. 3, the solvent is sprayed directly onto the target surface 50 to provide a solvent-wetted surface. The silicone adhesive collector may then be disposed directly on the solvent-wetted surface.

Figure 4:
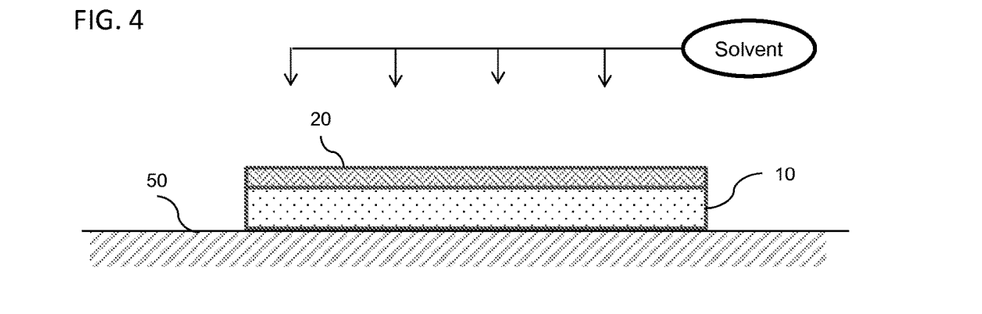
FIG. 4 illustrates another embodiment of a method of collecting a compound from a surface, wherein the solvent is disposed on a backing 20 of the silicon adhesive collector after the silicone adhesive collector has been adhered to the target surface.

In another embodiment as shown in FIG. 4, the silicone adhesive collector is adhered directly to the target surface 50. The solvent is then disposed on the backing of the silicon adhesive collector. The silicon adhesive collector may then be removed from the surface after a selected time.

In yet another embodiment, the procedure is as is disclosed except that the solvent is omitted to provide a dry collection method.

In yet another embodiment, a selected combination of solvents is used. For example the solvent may be a combination of isopropanol and ethyl acetate, or a combination of ethyl acetate and hexane. The solvent mixtures can be selected to provide a selected combination of properties, and can be selected based on the targeted compound for collection and the properties of the surface being tested. For example, if a targeted compound for collection is known to be soluble in alcohols, an alcohol such as methanol, ethanol, or isopropanol, or combination thereof can be used. Alternatively, if the surface to be tested is known to be susceptible to damage from apolar hydrocarbons, a polar solvent such as ethanol can be used.

The invention is further illustrated by the following examples, which are non-limiting prophetic examples.

EXAMPLES

Examples 1 to 7: Preparation of Collectors

An ethylenically unsaturated polydimethylsiloxane and an —SiH containing polydimethylsiloxane will be combined with a platinum catalyst to provide a polydimethylsiloxane silicone adhesive copolymer composition. The polydimethylsiloxane silicone adhesive copolymer composition will be cast onto the backings provided in Table 1 to provide a 2 millimeter thick layer of the composition on each backing. The cast compositions will then be cured at 100° C. for 20 minutes to provide the collectors of Examples 1 to 7.

TABLE 1

| Example | Backing Name | Backing Type | Backing Source |
|---|---|---|---|
| 1 | Elastosil film | Silicon elastomer | Wacker Silicones |
| 2 | PS Si 1033 | Silicone elastomer | Polymer Science, Inc. |
| 3 | CS Hyde | Silicone elastomer | CS Hyde Company |
| 4 | PS Urethane 1082 | Polyether polyurethane | Polymer Science, Inc. |
| 4 | Medifilm 437 | Aliphatic polyether polyurethane | Mylan Industries |
| 6 | Medifilm 426 | Hydrophilic polyurethane | Mylan Industries |
| 7 | Al foil | Aluminum | Aldrich |

For comparison, 100% cotton gauze is used in the Comparative Examples.

Evaluation of Collection Efficiency

Examples 8 to 14: Collection without Solvent

To evaluate the collection efficiency of each of the Examples and the gauze, parathion collection from a concrete brick will be evaluated. First, a concrete brick will be sprayed with a 0.01 weight percent (wt %) aqueous solution of parathion and allowed to dry at room temperature for 24 hours. Second, collectors according to Examples 1 to 7 and the gauze will be applied to the brick for 10 minutes. After the 10 minutes, each of the collectors will be removed and placed in a polyethylene bag to provide loaded collectors of Examples 8 to 14 and Comparative Example 1. Each collector will then be analyzed by gas chromatography-mass spectrometry (GC/MS) for parathion.

Examples 15 to 21: Collection with Hexane

Examples 15 to 21 and Comparative Example 2 will be the same as Examples 8 to 14, with the exception that each of the collectors and the gauze will be dipped in hexane prior to their application to the brick to provide loaded collectors of Examples 15 to 21 and Comparative Example 2

Results

GC/MS analysis of the collectors of Examples 8 to 21 will show that the collectors of Examples 15 to 21 recover more parathion than the collectors of Examples 8 to 14. The improved collection in Examples 15 to 21 will show that use of the collector in combination with a solvent, such as hexane, provides an unexpected improvement in collection efficiency.

The GC/MS analysis will also show that the collectors of Examples 8 to 14 recover more parathion than the gauze of Comparative Example 1. Also, the GC/MS analysis will show that the collectors of Examples 15 to 21 recover more parathion than the gauze of Comparative Example 2. Thus the GC/MS analysis will show that the silicone adhesive collectors provide unexpected improvement in collection efficiency when compared to gauze.

In addition, the GC/MS analysis will show that collectors including a polysiloxane backing, specifically the collectors of Examples 10 and 17, which will comprise the CS Hyde backing, provide an unexpected improvement in collection efficiency. While not wanting to be bound by theory, it is understood that there is a synergistic relationship between the polysiloxane backing and the silicone adhesive. It is theorized that the polysiloxane backing can contain the parathion, enhancing the ability of the silicone adhesive to collect the parathion.

"Alkyl" as used herein means a straight or branched chain, saturated, monovalent hydrocarbon group (e.g., methyl or hexyl).

"Alkenyl" means a straight or branched chain, monovalent hydrocarbon group having at least one carbon-carbon double bond (e.g., ethenyl (—HC=CH$_2$)).

"Cycloalkyl as used herein refers to a non-aromatic monovalent monocyclic or multicylic hydrocarbon group having at least three carbon atoms.

"Alkylaryl" means an alkyl group covalently linked to a substituted or unsubstituted aryl group that is linked to a compound (e.g., 2-methylphenyl).

"Allyl" means a group of the formula H$_2$C=CH—CH$_2$—.

"Aliphatic" means a saturated or unsaturated linear or branched hydrocarbon group. An aliphatic group may be an alkyl, alkenyl, or alkynyl group, for example.

"Hydrocarbon" means an organic compound having at least one carbon atom and at least one hydrogen atom, optionally substituted with one or more substituents where indicated.

"Substituted" means that the compound or group is substituted with at least one (e.g., 1, 2, 3, or 4) substituents that can be a hydroxyl (—OH), a C1-9 alkoxy, a C1-9 haloalkoxy, an oxo (=O), a nitro (—NO$_2$), a cyano (—CN), an amino (—NH$_2$), an azido (—N$_3$), an amidino (—C(=NH)NH$_2$), a hydrazino (—NHNH$_2$), a hydrazono (=N—NH$_2$), a carbonyl (—C(=O)—), a carbamoyl group (—C(O)NH$_2$), a sulfonyl (—S(=O)$_2$—), a thiol (—SH), a thiocyano (—SCN), a tosyl (CH$_3$C$_6$H$_4$SO$_2$—), a carboxylic acid (—C(=O)OH), a carboxylic C1 to C6 alkyl ester (—C(=O)OR wherein R is a C1 to C6 alkyl group), a carboxylic acid salt (—C(=O)OM) wherein M is an organic or inorganic anion, a sulfonic acid (—SO$_3$H$_2$), a sulfonic mono- or dibasic salt (—SO$_3$MH or —SO$_3$M$_2$ wherein M is an organic or inorganic anion), a phosphoric acid (—PO$_3$H$_2$), a phosphoric acid mono- or dibasic salt (—PO$_3$MH or —PO$_3$M$_2$ wherein M is an organic or inorganic anion), a C1 to C12 alkyl, a C3 to C12 cycloalkyl, a C2 to C12 alkenyl, a C5 to C12 cycloalkenyl, a C2 to C12 alkynyl, a C6 to C12 aryl, a C7 to C13 arylalkylene, a C4 to C12 heterocycloalkyl, or a C3 to C12 heteroaryl instead of hydrogen, provided that the substituted atom's normal valence is not exceeded. Combinations of substituents and/or variables are permissible provided that the substitutions do not significantly adversely affect synthesis or use of the compound.

"Vinyl" includes any group having terminal unsaturation (—CH$_2$=CH$_2$), including acrylate groups (—OC(O)CH=CH$_2$) and methacrylate (—OC(O)(CH$_3$)=CH$_2$) groups.

The disclosed embodiments may be embodied in many different forms, and this disclosure should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for collecting a compound from a surface, the method comprising:
    providing a silicone adhesive collector comprising a silicone adhesive layer directly on a backing, wherein the silicone adhesive layer comprises
        a cured silicone adhesive product of a composition comprising an ethylenically unsaturated organopolysiloxane, an SiH containing organopolysiloxane, and a hydrosilylation catalyst, wherein the SiH containing organopolysiloxane comprises
        (a) an organopolysiloxane comprising at least three —SiH groups per molecule, a $R^1{}_2XSiO_{1/2}$ terminal group, an $R^1HSiO$— unit, and optionally an $R^1{}_2SiO_{2/2}$— unit, and
        (b) an —SiH terminated organopolysiloxane comprising a $R^1HSiO_{1/2}$ terminal group and an $R^1{}_2SiO_{2/2}$— unit,
        wherein in (a) and (b) each $R^1$ may the same or different and is a $C_1$ to $C_8$ alkyl, a $C_1$ to $C_8$ perfluoroalkyl, or a $C_6$ to $C_8$ aryl, and X is H or $R^1$;
    contacting the silicone adhesive collector and a first solvent to provide a wetted collector, wherein the first solvent comprises an alcohol, an aldehyde, a ketone, an ester, an ether, an amide, a hydrocarbon, acetonitrile, a sulfoxide, a sulfone, or a combination thereof;
    contacting the silicone adhesive layer of the silicone adhesive collector and a surface to be analyzed to provide a loaded collector; and
    removing the loaded collector from the surface to collect the compound.

2. The method of claim 1, wherein the contacting of the silicone adhesive collector and the first solvent is prior to the contacting of the silicone adhesive collector and the surface to be analyzed.

3. The method of claim 2, wherein the contacting of the silicone adhesive collector and the first solvent comprises dipping the silicone adhesive collector in the first solvent.

4. The method of claim 1, wherein the contacting of the silicone adhesive collector and the first solvent is after the contacting of the silicone adhesive layer and the surface to be analyzed.

5. The method of claim 1, further comprising disposing the first solvent on the surface to be analyzed prior to the contacting of the silicone adhesive layer and the surface to be analyzed.

6. The method of claim 1, wherein the first solvent comprises a hydrocarbon.

7. The method of claim 1, wherein the first solvent comprises an alcohol, an ester, a ketone, an olefin, or a combination thereof.

8. The method of claim 1, wherein the backing is permeable to the first solvent.

9. The method of claim 8, wherein the backing comprises a silicone elastomer, a silicon rubber, polytetrafluoroethylene, a polyester, a polyamine, a polyolefin, or a combination thereof.

10. The method of claim 1, wherein the backing is non-permeable to the first solvent.

11. The method of claim 10, wherein the non-permeable backing comprises a metal, a glass, a polymer, or a combination thereof.

12. The method of claim 1, wherein the silicone adhesive is in the form of a gel having a viscosity of 100,000 centiPoise to 5,000,000 centiPoise.

13. The method of claim 1, wherein the composition has
    an RH:Alk in the range of 0.1 to 10, wherein RH:Alk is a ratio of a total number of —SiH groups in the organopolysiloxane (a) and the diorganohydrogensiloxy-terminated polydiorganosiloxane (b) combined to the number of Si-alkenyl groups in the composition; and
    an RH(C) of 10% to 99%, wherein RH(C) is the mole percent of the —SiH groups provided by the —SiH terminated organopolysiloxane (b) relative to the total moles of —SiH groups in the organopolysiloxane (a) and the —SiH terminated organopolysiloxane (b).

14. The method of claim 13, wherein the silicone adhesive has an RH:Alk of 0.8 to 2 and an RH(C) of 80% to 99%.

15. The method of claim 14, wherein the silicone adhesive has an RH:Alk of 0.8 to 1.7 a RH(C) of 85% to 95%.

16. The method of claim 1, wherein the silicone adhesive layer further comprises a second solvent, wherein the first solvent and the second solvent are different.

17. The method of claim 1, wherein the silicon adhesive layer has a thickness of 0.1 millimeter to 10 millimeters.

18. The method of claim 1, wherein the silicone adhesive has a tack of 5 millimeters to 300 millimeters, when determined by the PSTC-6 Tack Rolling Ball method as defined by the Pressure Sensitive Tape Council and using a steel ball.

19. The method of claim 1, wherein the silicone adhesive has a tack of 5 grams-force-inch to 1500 grams-force-inch, when determined on concrete brick according to the PSTC-101 Peel Adhesion of Pressure Sensitive Tape method as defined by the Pressure Sensitive Tape Council.

20. The method of claim 1, further comprising removing a release layer disposed on the silicone adhesive to expose the silicone adhesive.

21. The method of claim 1, wherein the silicone adhesive collector is contacted to the surface to be analyzed for 1 second to 100 hours.

22. A method of analyzing a surface for a compound, the method comprising:
    collecting a compound from a surface by the method of claim 1; and
    analyzing the silicone adhesive collector to determine a content of the compound to analyze the surface for the compound.

23. A system for collecting a chemical compound from a surface, the system comprising:
    a silicone adhesive collector comprising
        a backing, and a silicone adhesive layer disposed directly on the backing, wherein the silicone adhesive layer comprises
  a cured silicone adhesive product of a composition comprising an ethylenically unsaturated organopolysiloxane, an —SiH containing organopolysiloxane, and a hydrosilylation catalyst, wherein the —SiH containing organopolysiloxane comprises
    (a) an organopolysiloxane comprising at least three —SiH groups per molecule, a $R^1_2XSiO_{1/2}$ terminal group, an $R^1HSiO$— unit, and optionally an $R^1_2SiO_{2/2}$— unit, and
    (b) an —SiH terminated organopolysiloxane comprising a $R^1HSiO_{1/2}$ terminal group and an $R^1_2SiO_{2/2}$— unit,
    wherein in (a) and (b) each $R^1$ may the same or different and is a $C_1$ to $C_8$ alkyl, a $C_1$ to $C_8$ perfluoroalkyl, or a $C_6$ to $C_8$ aryl, and X is H or $R^1$;
a first solvent, wherein the first solvent comprises an alcohol, an aldehyde, a ketone, an ester, an ether, an amide, a hydrocarbon, acetonitrile, a sulfoxide, a sulfone, or a combination thereof; and
instructions to dispose the first solvent on the silicone adhesive collector, the surface, or a combination thereof.

24. The system of claim 23, wherein the instructions instruct disposing the first solvent on the silicone adhesive layer, the surface, or a combination thereof prior to contacting the silicone adhesive layer and the surface.

25. The system of claim 23, further comprising a second solvent in the silicone adhesive layer.

26. The system of claim 23, further comprising a release layer on the silicone adhesive layer.

27. The system of claim 23, where a tack of the silicone adhesive layer is sufficient to allow the collector to adhere to a vertical surface.

28. The system of claim 23, wherein the backing is non-tacky.

29. The system of claim 23, wherein the backing is permeable to the first solvent.

30. The system of claim 23, wherein the first solvent comprises an alcohol, an ester, an olefin, or a combination thereof.

31. The system of claim 23, wherein the silicone adhesive has a tack of 5 millimeters to 300 millimeters, when determined by the PSTC-6 Tack Rolling Ball method as defined by the Pressure Sensitive Tape Council and using a steel ball.

32. The system of claim 23, wherein the silicone adhesive has a tack of 5 grams-force-inch to 1500 grams-force-inch, when determined on concrete brick according to the PSTC-101 Peel Adhesion of Pressure Sensitive Tape method as defined by the Pressure Sensitive Tape Council.

33. The system of claim 29, wherein the backing comprises a silicone elastomer, a silicon rubber, polytetrafluoroethylene, a polyester, a polyamine, a polyolefin, or a combination thereof.

34. The system of claim 23, wherein the backing is non-permeable to the first solvent.

35. The system of claim 34, wherein the non-permeable backing comprises a metal, a glass, a polymer, or a combination thereof.

* * * * *